United States Patent
Kasagi

(10) Patent No.: US 8,852,563 B2
(45) Date of Patent: Oct. 7, 2014

(54) COSMETIC

(71) Applicant: FUJIFILM Corporation, Tokyo (JP)

(72) Inventor: Minako Kasagi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/261,740

(22) Filed: Apr. 25, 2014

(65) Prior Publication Data

US 2014/0234426 A1 Aug. 21, 2014

Related U.S. Application Data

(63) Continuation of application No. PCT/JP2012/077913, filed on Oct. 29, 2012.

(30) Foreign Application Priority Data

Oct. 31, 2011 (JP) ................. 2011-239728

(51) Int. Cl.
- *A61K 8/29* (2006.01)
- *A61Q 17/04* (2006.01)
- *A61K 8/49* (2006.01)
- *A61K 8/35* (2006.01)

(52) U.S. Cl.
CPC .............. *A61K 8/4973* (2013.01); *A61Q 17/04* (2013.01); *A61K 8/35* (2013.01)
USPC ......... 424/59; 424/70.1; 424/70.9; 424/70.16

(58) Field of Classification Search
USPC ................. 424/59, 70.1, 70.9, 70.16
See application file for complete search history.

(56) References Cited

U.S. PATENT DOCUMENTS

2012/0156149 A1 6/2012 Yamaguchi et al.

FOREIGN PATENT DOCUMENTS

| JP | 7-577936 A | 10/1995 |
|---|---|---|
| JP | 9-286928 A | 11/1997 |
| JP | 2000-086446 A | 3/2000 |
| JP | 2011-068567 A | 4/2011 |
| WO | WO 2010/098249 A1 | 9/2010 |

OTHER PUBLICATIONS

STIC Search Report dated May 21, 2014.*
English translation of the Japanes Patent # JP, 09-286928, A (1997).*
International Search Report issued in PCT/JP2012/077913, mailed on Jan. 29, 2013.
Written Opinion issued in PCT/JP2012/077913, mailed on Jan. 29, 2013.

* cited by examiner

*Primary Examiner* — Eisa Elhilo
(74) *Attorney, Agent, or Firm* — Birch, Stewart, Kolasch & Birch, LLP

(57) ABSTRACT

A cosmetic, includes: a composite powder containing titanium oxide and 4-tert-butyl-4-methoxybenzoylmethane and having an average particle diameter of less than 1 µm; and sorbitan fatty acid ester represented by the following Formula (I): wherein, in Formula (I), $R^1$ to $R^4$ each independently represent $-(CH_2)_nCOOH$, $-(CH_2)_nOH$, $-R^5$, or $-OR^6$; $R^5$ represents an aliphatic group having from 1 to 22 carbon atoms; $R^6$ represents an acyl group having from 10 to 22 carbon atoms; n represents 0 or an integer from 1 to 29; and at least one of $R^1$ to $R^4$ represents $-OR^6$.

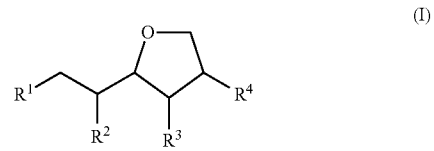

(I)

13 Claims, No Drawings

COSMETIC

CROSS-REFERENCE TO RELATED APPLICATIONS

This application is a continuation application of International Application No. PCT/JP2012/077913, filed Oct. 29, 2012, the disclosure of which is incorporated herein by reference in its entirety. Further, this application claims priority from Japanese Patent Application No. 2011-239728, filed Oct. 31, 2011, the disclosure of which is incorporated herein by reference in their entirety.

TECHNICAL FIELD

The present invention relates to a cosmetic.

BACKGROUND ART

Various organic ultraviolet absorbers have been used in order to impart an ultraviolet blocking effect to cosmetics. In particular, ultraviolet shielding powders, in which inorganic powders and ultraviolet absorbers of organic compounds are formed as a composite, are known.

For example, International Publication (WO) No. 2010/098249 discloses a composite powder in which the surface of a base material powder is coated with an organic compound having an ultraviolet absorbing ability. It is described in WO 2010/098249 that the composite powder is a composite powder in which an organic compound having an ultraviolet absorbing ability and an inorganic pigment having an ultraviolet scattering ability are formed as a composite, and is a powder type capable of being stably blended into a cosmetic, maintains a high ultraviolet absorbing effect, and is an organic ultraviolet absorber exhibiting favorable dispersibility. As this kind of composite powder, WO 2010/098249 discloses a composite powder in which a surface of fine particles of titanium oxide is coated with butyl methoxydibenzoylmethane.

In addition, Japanese Patent Application Laid-Open (JP-A) No. H07-277936 discloses an ultraviolet shielding powder containing, in predetermined amounts: an ultraviolet absorber such as 4-tert-butyl-4-methoxybenzoylmethane; wax and/or an oil gelling agent each of which has a gelling ability, such as dextrin fatty acid ester; and a powder such as titanium oxide. It is described that the ultraviolet shielding powder is an ultraviolet shielding powder in which an oily component containing an ultraviolet absorber is adsorbed to a powder together with wax and/or an oil gelling agent, and does not cause daily variation even when blended into a hydrous-system cosmetic, and thus a stable cosmetic with excellent use sensation and usability can be obtained, and JP-A No. H07-277936 discloses an ultraviolet shielding powder having a particle diameter of from 15 μm to 50 μm.

JP-A No. 2011-68567 discloses a sunscreen cosmetic, in which a UVA absorber such as 4-tert-butyl-4-methoxybenzoylmethane is blended with a given spherical resin powder such as ultrafine particles of titanium oxide.

SUMMARY OF INVENTION

Among the ultraviolet shielding powders described above, however, there are cases in which the composite powder in which the surface of fine particles of titanium oxide is coated with butyl methoxydibenzoylmethane absorbs or releases oily components in an emulsion type cosmetic when the composite powder is blended into the emulsion type cosmetic. As a result, there are cases in which changes in the viscosity of the cosmetic, or deterioration in the use sensation such with the occurrence of stickiness or a lack of appropriate spreading, occur. In addition, there are cases in which the ultraviolet absorber in the composite powder dissolves over time or recrystallizes in the preparation. As described above, the viscosity stability and use sensation of the cosmetic are not satisfactory when a composite powder having a high ultraviolet shielding effect is blended into an emulsion type cosmetic.

An object of the invention, in view of such circumstances, is to provide a cosmetic exhibiting a high ultraviolet shielding effect, favorable viscosity stability, and a favorable use sensation.

The invention is as follows.

[1] A cosmetic, comprising: a composite powder containing titanium oxide and 4-tert-butyl-4-methoxybenzoylmethane and having an average particle diameter of less than 1 μm and a sorbitan fatty acid ester represented by the following Formula (I).

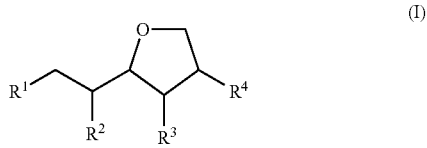

wherein, in Formula (I), $R^1$ to $R^4$ each independently represent $-(CH_2)_nCOOH$, $-(CH_2)_nOH$, $-R^5$, or $-OR^6$; $R^5$ represents an aliphatic group having from 1 to 22 carbon atoms; $R^6$ represents an acyl group having from 10 to 22 carbon atoms; n represents 0 or an integer from 1 to 29, and at least one of $R^1$ to $R^4$ represents $-OR^6$.

[2] The cosmetic according to [1], wherein the composite powder comprises a surface treatment layer, containing the 4-tert-butyl-4-methoxybenzoylmethane, on a surface of the titanium oxide.

[3] The cosmetic according to [1] or [2], wherein $R^6$ in Formula (I) represents an acyl group having from 10 to 20 carbon atoms.

[4] The cosmetic according to any one of [1] to [3], wherein the sorbitan fatty acid ester includes two or more sorbitan fatty acid esters each represented by Formula (I).

[5] The cosmetic according to any one of [1] to [4], wherein $R^6$ in Formula (I) is a group selected from the group consisting of a branched saturated aliphatic acyl group, a linear unsaturated aliphatic acyl group, and a branched unsaturated aliphatic acyl group, and a total carbon number of the acyl group is from 14 to 18.

[6] The cosmetic according to any one of [1] to [5], wherein the sorbitan fatty acid ester includes two or more sorbitan fatty acid esters each represented by Formula (I), in each of which the number of $-OR^6$ is different from one another.

[7] The cosmetic according to any one of [1] to [6], wherein $R^6$ in Formula (I) represents a branched saturated aliphatic acyl group having a total carbon number of from 14 to 18 or a linear unsaturated aliphatic acyl group having a total carbon number of from 14 to 18.

[8] The cosmetic according to any one of [1] to [7], wherein the sorbitan fatty acid ester is at least one selected from the group consisting of sorbitan sesquioleate and sorbitan sesquiisostearate.

[9] The cosmetic according to any one of [1] to [8], further comprises an oil absorbing powder.

[10] The cosmetic according to [9], wherein the oil absorbing powder is at least one powder selected from the group consisting of a porous silica powder, a crosslinked silicone powder, a porous nylon powder, a polymethyl methacrylate powder, and corn starch.

[11] The cosmetic according to any one of [1] to [10], wherein a content of the sorbitan fatty acid ester is from 0.01% by mass to 20% by mass with respect to a total mass of the cosmetic.

[12] The cosmetic according to any one of [1] to [11], wherein a content of the sorbitan fatty acid ester is from 0.0001 times to 150 times, the amount on a mass basis with respect to a content of the composite powder.

[13] The cosmetic according to any one of [1] to [12], being a sunscreen cosmetic.

[14] The cosmetic according to any one of [1] to [7] and [9] to [13], wherein the sorbitan fatty acid ester is at least one selected from the group consisting of:

(1) a sorbitan fatty acid ester, wherein, in Formula (I), one of $R^1$ to $R^4$ is —$OR^6$, wherein $R^6$ is a linear unsaturated aliphatic acyl group, a branched saturated aliphatic acyl group, or a branched unsaturated aliphatic acyl group; and the remaining three of $R^1$ to $R^4$ are each —OH groups;

(2) a sorbitan fatty acid ester, wherein, in Formula (I), one of $R^1$ to $R^4$ is —$OR^6$, wherein $R^6$ is a linear unsaturated aliphatic acyl group, a branched saturated aliphatic acyl group, or a branched unsaturated aliphatic acyl group; and the remaining three of $R^1$ to $R^4$ are each —OH groups;

(3) a sorbitan fatty acid ester, wherein, in Formula (I), two of $R^1$ to $R^4$ are each —$OR^6$, wherein the two $R^6$s are the same as each other and are both linear unsaturated aliphatic acyl groups, branched saturated aliphatic acyl groups, or branched unsaturated aliphatic acyl groups; and the remaining two of $R^1$ to $R^4$ are each —OH groups;

(4) a sorbitan fatty acid ester, wherein, in Formula (I), two of $R^1$ to $R^4$ are each —$OR^6$, wherein the two $R^6$s are different from each other and are each a linear unsaturated aliphatic acyl group, a branched saturated aliphatic acyl group, or a branched unsaturated aliphatic acyl group; and the remaining two of $R^1$ to $R^4$ are each —OH groups; and (5) a sorbitan fatty acid ester, wherein, in Formula (I), three of $R^1$ to $R^4$ are each —$OR^6$, wherein all three $R^6$s are linear unsaturated aliphatic acyl groups, branched saturated aliphatic acyl groups, or branched unsaturated aliphatic acyl groups; and the remaining one of $R^1$ to $R^4$ is a —OH group.

[15] The cosmetic according to any one of [1] to [7] and [9] to [14], wherein the sorbitan fatty acid ester is at least one selected from the group consisting of sorbitan monolaurate, sorbitan monopalmitate, sorbitan monostearate, sorbitan monooleate, sorbitan monoisostearate, sorbitan sesquicaprylate, sorbitan sesquioleate, sorbitan sesquistearate, sorbitan sesquiisostearate, sorbitan trioleate, sorbitan tristearate, sorbitan triisostearate, diglycerol sorbitan tetraethylhexanoate, diglycerol sorbitan pentaethylhexanoate, and coconut fatty acid sorbitan.

[16] The cosmetic according to any one of [9] to [15], wherein the oil absorbing powder is at least one selected from the group consisting of silica, silica silylate, dimethyl silica silylate, silica dimethicone silylate, a silicone gel powder, a silicone rubber powder, a silicone resin powder, a silicone elastomer, nylon, nylon-6, nylon-11, nylon-12, a nylon-12/6/66 copolymer, nylon-6/12, nylon-66, PMMA, a methyl methacrylate crosspolymer, a (methyl methacrylate/glycol dimethacrylate) crosspolymer, a (methyl methacrylate/acrylonitrile) copolymer, a (polymethyl methacrylate/dimethyl polysiloxane graft acrylic resin) copolymer, and an (ethylhexyl acrylate/methyl methacrylate) copolymer.

According to the invention, a cosmetic exhibiting a high ultraviolet shielding effect, favorable viscosity stability, and a favorable use sensation can be provided.

DESCRIPTION OF EMBODIMENTS

The cosmetic of the invention is a cosmetic containing a composite powder which contains titanium oxide and 4-tert-butyl-4-methoxybenzoylmethane and has an average particle diameter of less than 1 μm; and a sorbitan fatty acid ester represented by the following Formula (I).

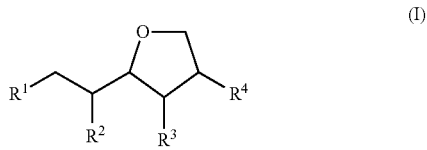

In Formula (I), $R^1$ to $R^4$ each independently represent —$(CH_2)_n$COOH, —$(CH_2)$OH, —$R^5$, or —$OR^6$; $R^5$ represents an aliphatic group having from 1 to 22 carbon atoms; $R^6$ represents an acyl group having from 10 to 22 carbon atoms; n represents 0 or an integer from 1 to 29; and at least one of $R^1$ to $R^4$ represents —$OR^6$.

The cosmetic according to the invention contains a predetermined sorbitan fatty acid ester, and thus the viscosity stability of the cosmetic containing the predetermined composite powder in combination is improved and a use sensation is also improved. As a result, a cosmetic exhibiting excellent viscosity stability and an excellent use sensation without impairing the high ultraviolet shielding performance brought by the composite powder can be provided.

The term "process" in the present specification includes not only an independent process but also a case where a process is not clearly distinguished from other processes as long as the intended purpose of the process is achieved.

In addition, the term "~(to)" in the present specification denotes a range including the numerical values written before and after "~(to)" as the minimum value and the maximum value, respectively.

Moreover, in a case where a plurality of substances corresponding to each of the components in the composition is present, the amount of each of the components in the composition in the present specification means the total amount of a plurality of substances present in the composition, unless otherwise stated.

Hereinafter, the invention is described.

The cosmetic according to the invention is a cosmetic containing a composite powder which contains titanium oxide and 4-tert-butyl-4-methoxybenzoylmethane and has an average particle diameter of less than 1 μm; and a sorbitan fatty acid ester represented by Formula (I) above.

The cosmetic is preferably in an emulsion form. The emulsion form is not particularly limited, and may be a W/O type or an O/W type.

<Composite Powder>

The composite powder is a composite powder which contains titanium oxide and 4-tert-butyl-4-methoxybenzoylmethane and has an average particle diameter of less than 1 μm. The composite powder exhibits high ultraviolet shielding performance since 4-tert-butyl-4-methoxybenzoylmethane is contained.

The average particle diameter of the composite powder is required to be less than 1 μm. When the average particle diameter of the composite powder is 1 μm or more, a cosmetic is colored by the composite powder itself and the so-called white powder residue occurs. The average particle diameter of the composite powder is preferably from 1 nm to 500 nm and more preferably from 3 nm to 100 nm, from the viewpoints of ultraviolet shielding performance and a use sensation.

The particle diameter of the composite powder is the value obtained by dispersing powder, taking the image of 1000 or more particles using a transmission electron microscope, performing image treatment of individual particles in which the images thereof have been taken, with an image analysis type particle size distribution measuring apparatus, and measuring the equivalent circle diameter. When a commercially available product is used, the average particle diameter of commercially available product may be adopted as it is.

The present composite powder is preferably a composite powder having a surface treatment layer containing 4-tert-butyl-4-methoxybenzoylmethane as an ultraviolet absorber, on a surface of titanium oxide. The bonding mode between the surface treatment layer and titanium oxide is not particularly limited as long as 4-tert-butyl-4-methoxybenzoylmethane and titanium oxide behave integrally. The bonding mode may be a chemical bond such as a covalent bond or may be a nonchemical bond such as adsorption.

In addition, fatty acid and aluminum hydroxide can be contained in the surface treatment layer. When the fatty acid is contained in the surface treatment layer, the surface of the powder can be hydrophobic, and when the aluminum hydroxide is contained in the surface treatment layer, titanium oxide can be inactivated.

As the composite powder, examples thereof include the composite powders described in WO 2010/098249. In addition, as the composite powder, a commercially available product can be used and examples thereof include HXMT-100ZA manufactured by TAYCA Corporation.

The content of the composite powder in the cosmetic is preferably from 0.1% by mass to 50% by mass, more preferably from 0.5% by mass to 25% by mass, and still more preferably from 1% by mass to 15% by mass, with respect to the total mass of the cosmetic. When the content of the composite powder is 0.1% by mass or more, an ultraviolet blocking effect can be obtained and when the content is 50% by mass or less, the composite powder can be stably blended in the formula.

The average primary particle diameter of titanium oxide is preferably from 1 nm to 90 nm, and more preferably from 5 nm to 50 nm, from the viewpoint of ultraviolet shielding performance and transparency of the cosmetic. The average primary particle diameter of titanium oxide is the value obtained by dispersing titanium oxide, taking the image of 1000 or more particles with a transmission electron microscope, performing image treatment of individual particles in which the images thereof have been taken, with an image analysis type particle size distribution measuring apparatus, and measuring the equivalent circle diameter. When a commercially available product is used, the average primary particle diameter of commercially available product may be adopted as it is.

When the composite powder is blended into the cosmetic, slurry may be prepared using a dispersion medium such as silicone oil, and then the composite powder in a slurry form may be blended with other components, for example.

The content of the composite powder in the slurry is not particularly limited, and generally, is preferably from 10% by mass to 80% by mass and more preferably from 20% by mass to 60% by mass, with respect to the total mass of the slurry. When the content is 10% by mass or more, the composite powder can be stably blended into the formulation, and the content is still more preferably from 20% by mass to 60% by mass.

<Sorbitan Fatty Acid Ester>

The sorbitan fatty acid ester is a compound represented by Formula (I) above.

In the formula, $R^1$ to $R^4$ each independently represent —$(CH_2)_n$COOH, —$(CH_2)_n$OH, —$R^5$, or —$OR^6$, and may be the same as or different from one another, but at least one of $R^1$ to $R^4$ is —$OR^6$. The sorbitan fatty acid ester is an ester of one or more fatty acids and a sorbitol derivative, and does not contain a hydrophilic monovalent or divalent substituent such as polyoxyethylene or the like, from the viewpoint of the viscosity stability of the cosmetic.

The sorbitan fatty acid ester may be contained in the cosmetic as a single compound, or a combination of two or more sorbitan fatty acid esters having different $R^1$ to $R^4$ from each other may be used.

When the sorbitan fatty acid ester is a mixture of more than one kind, the mixture may be a mixture of more than one kind having different kinds of $R^1$ to $R^4$. The mixture of more than one kind preferably has different bonding positions, numbers or kinds of at least one —$OR^6$ at $R^1$ to $R^4$, or combinations thereof. As such a mixture of more than one kind, examples thereof include a mixture having different numbers of —$OR^6$ in the compound (a monoester derivative, a diester derivative, or a triester derivative or the like, of fatty acid), different kinds of $R^6$ (for example, a combination having different carbon numbers of $R^6$, and a combination having different numbers and/or positions of a double bond), or different combinations of these. Among them, a combination of sorbitan fatty acid esters having different numbers of —$OR^6$ in the compound, for example, sesquifatty acid sorbitan, is preferable, as the sorbitan fatty acid ester from the viewpoints of the viscosity stability and a use sensation.

In the formula, n is 0 or an integer of from 1 to 29. When n is 30 or more, the viscosity stability is impaired. n is preferably 0 or from 10 to 22, and more preferably 0, in terms that the viscosity stability can be improved, and from the viewpoints of the viscosity stability and a use sensation.

The aliphatic group in $R^5$ may be a saturated or unsaturated aliphatic group, an unsaturated aliphatic group having an unsaturated bond number of one or two or more, or an aliphatic group having a straight chain or a branched chain. In addition, as the aliphatic group, a cyclic structure may be contained.

$R^5$ represents an aliphatic group having from 1 to 22 carbon atoms. The viscosity stability or a use sensation cannot be improved when an aliphatic group having 23 or more carbon atoms. $R^5$ is preferably an aliphatic group having from 10 to 20 carbon atoms and more preferably an aliphatic group having from 12 to 14 carbon atoms, from the viewpoints of the viscosity stability and a use sensation.

The acyl group in $R^6$ may be an aliphatic acyl group, and the aliphatic acyl group may be a saturated or unsaturated aliphatic acyl group, an unsaturated aliphatic acyl group having an unsaturated bond number of one or two or more, or an aliphatic acyl group having a straight chain or a branched chain.

The acyl group of $R^6$ is preferably a linear saturated aliphatic acyl group, a branched saturated aliphatic acyl group, a linear unsaturated aliphatic acyl group, or a branched unsaturated aliphatic acyl group, and more preferably a branched saturated aliphatic acyl group, a linear unsaturated aliphatic acyl group, or a branched unsaturated aliphatic acyl group, in terms of the viscosity stability and a use sensation. In addition, $R^6$ is required to have from 10 to 22 carbon atoms, and when the carbon number is 9 or less or 23 or more, improvement in the viscosity stability or a use sensation is not obtained. $R^6$ is preferably an acyl group having a total carbon number of from 10 to 20 and more preferably an acyl group having a total carbon number of from 14 to 18, from the viewpoints of the viscosity stability and a use sensation.

It is still more preferable that —$OR^6$ is a branched saturated aliphatic acyl group, a linear unsaturated aliphatic acyl group, or a branched unsaturated aliphatic acyl group, and the total carbon number of the aliphatic acyl group is from 10 to 20 and more preferably from 14 to 18, in terms of the viscosity stability and a use sensation.

As —$(CH_2)_n COOH$, examples thereof may include a carboxyl group, a methylcarboxyl group, and an ethylcarboxyl group.

As —$(CH_2)_n OH$, examples thereof include a hydroxyl group, —$CH_2OH$, and —$(CH_2)_2OH$, and a hydroxyl group or the like is preferable.

As —$R^5$, examples thereof may include a methyl group, an ethyl group, a propyl group, a methylpropyl group, a dimethylethyl group, a pentyl group, a methylbutyl group, an ethylpropyl group, a hexyl group, a methylpentyl group, a dimethylbutyl group, an ethylbutyl group, a heptyl group, an octyl group, an ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a docosyl group, a vinyl group, an allyl group, and an isopropenyl group.

As —$R^6$, examples thereof may include a decanyl group, a lauroyl group, a myristoyl group, a palmitoryl group, a stearoyl group, an oleoyl group, a linoleyl group, a linolenoyl group, an isostearoyl group, a behenoyl group, an icosapentaenoyl group, and a docosahexaenoyl group. A myristoyl group, a palmitoryl group, a stearoyl, an oleoyl group, an isostearoyl group, an arachidyl group, and the like are preferable.

The $R^1$ to $R^4$ other than —$OR^6$ is preferably a carboxyl group or a hydroxyl group and more preferably a hydroxyl group, in terms of in the ability to improve the emulsion stability (viscosity stability).

The sorbitan fatty acid ester is preferably any of the following sorbitan fatty acid esters:

(1) a sorbitan fatty acid ester, wherein, in Formula (I), any one of $R^1$ to $R^4$ is —$OR^6$, wherein $R^6$ is a linear unsaturated aliphatic acyl group, a branched saturated aliphatic acyl group, or a branched unsaturated aliphatic acyl group, and the remaining three of $R^1$ to $R^4$ are —OH groups;

(2) a sorbitan fatty acid ester, wherein, in Formula (I), any one of $R^1$ to $R^4$ is —$OR^6$, wherein $R^6$ is a linear unsaturated aliphatic acyl group, a branched saturated aliphatic acyl group, or a branched unsaturated aliphatic acyl group, and the remaining three of $R^1$ to $R^4$ are —OH groups;

(3) a sorbitan fatty acid ester, wherein, in Formula (I), any two of $R^1$ to $R^4$ are —$OR^6$, wherein the two $R^6$s are the same as each other and are both linear unsaturated aliphatic acyl groups, branched saturated aliphatic acyl groups, or branched unsaturated aliphatic acyl groups, and the remaining two of $R^1$ to $R^4$ are —OH groups;

(4) a sorbitan fatty acid ester, wherein, in Formula (I), any two of $R^1$ to $R^4$ are —$OR^6$, wherein the two $R^6$s are different from each other and are each a linear unsaturated aliphatic acyl group, a branched saturated aliphatic acyl group, or a branched unsaturated aliphatic acyl group, and the remaining two of $R^1$ to $R^4$ are —OH groups; and (5) a sorbitan fatty acid ester, wherein, in Formula (I), any three of $R^1$ to $R^4$ are —$OR^6$, wherein all three of $R^6$s are linear unsaturated aliphatic acyl groups, branched saturated aliphatic acyl groups, or branched unsaturated aliphatic acyl groups, and the remaining one of $R^1$ to $R^4$ is a —OH group.

In (1) to (5) above, one or a plurality of —$OR^6$ present in Formula (I) is still more preferably a branched saturated aliphatic acyl group having a total carbon number of from 14 to 18 or a branched unsaturated aliphatic acyl group having a total carbon number of from 14 to 18.

As the sorbitan fatty acid ester, examples thereof may include sorbitan monolaurate, sorbitan monopalmitate, sorbitan monostearate, sorbitan monooleate, sorbitan monoisostearate, sorbitan sesquicaprylate, sorbitan sesquioleate, sorbitan sesquistearate, sorbitan sesquiisostearate, sorbitan trioleate, sorbitan tristearate, sorbitan triisostearate, diglycerol sorbitan tetraethylhexanoate, diglycerol sorbitan pentaethylhexanoate, and coconut fatty acid sorbitan. Sorbitan sesquicaprylate, sorbitan sesquioleate, sorbitan sesquistearate, sorbitan sesquiisostearate, sorbitan trioleate, sorbitan tristearate, sorbitan triisostearate, and the like are preferable, and sorbitan sesquioleate or sorbitan sesquisostearate is still more preferable, from the viewpoints of the viscosity stability and a use sensation.

In the invention, these sorbitan fatty acid esters can be used singly or in combination of two or more thereof.

The content of the sorbitan fatty acid ester is preferably from 0.01% by mass to 20% by mass, more preferably from 0.01% by mass to 15% by mass, still more preferably from 0.05% by mass to 10% by mass, and still more preferably from 0.1% by mass to 5% by mass, with respect to the total mass of the cosmetic, from the viewpoints of the viscosity stability and a use sensation. When the content is 0.01% by mass or more, the viscosity stability tends to be improved, and when the content is 20% by mass or less, emulsion dispersibility of the formulation tends to be improved.

In addition, the content of the sorbitan fatty acid ester is preferably from 0.0001 times to 150 times, more preferably from 0.0005 times to 50 times, further more preferably from 0.001 times to 5 times, still more preferably from 0.001 times to 1 time, and particularly preferably from 0.001 times to 0.5 times, the amount on a mass basis, with respect to the content of the composite powder. When the content of the sorbitan fatty acid ester is 0.0001 times or higher with respect to the content of the composite powder, the viscosity stability tends to be improved, and when the content is 50 times or lower, the dispersibility of the composite powder tends to be improved.

<Surfactant>

The cosmetic can contain a surfactant other than the sorbitan fatty acid ester.

The surfactant may be any of a nonionic surfactant, an anionic surfactant, and a cationic surfactant. Examples of the ionic surfactant include an alkyl sulfonate, an alkyl sulfate, a monoalkyl phosphate, and lecithin. Examples of the nonionic surfactant include a glycerin fatty acid ester, an organic acid monoglyceride, a polyglycerin fatty acid ester, a propylene glycol fatty acid ester, a polyglycerin condensed ricinoleic acid ester, a sucrose fatty acid ester, a polyethylene glycol fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, polyoxyethylene castor oil, polyoxyethylene cured castor oil, PEG-9 polydimethylsiloxane ethyl dimethicone, and a (dimethicone/(PEG-10/15)) crosspolymer. Among these, polyoxyethylene cured castor oil is preferable in terms that other oil components which are blended in for moisture retaining property can be stably dispersed.

The content of the surfactant other than the sorbitan fatty acid ester as the total amount with the sorbitan fatty acid ester in the cosmetic is preferably from 0.01% by mass to 20% by mass, more preferably from 0.1% by mass to 10% by mass, and still more preferably from 0.5% by mass to 5% by mass, with respect to the total mass of the cosmetic. When the content of the surfactant other than the sorbitan fatty acid ester is 0.01% by mass or more, the viscosity stability tends to be improved, and when the content is 20% by mass or less, the dispersibility of the composite powder tends to be improved.

<Fatty Acid>

The cosmetic can contain a fatty acid. By inclusion of a fatty acid, the viscosity stability and a use sensation can be further improved.

The fatty acid may be a saturated or unsaturated fatty acid, and may be a linear or branched fatty acid. The total carbon number of the fatty acid is not particularly limited, and is preferably from 8 to 20, more preferably from 10 to 18, from the viewpoints of the viscosity stability and a use sensation. Among them, a linear unsaturated fatty acid, a branched saturated fatty acid, or a branched unsaturated fatty acid is preferable from the viewpoints of the viscosity stability and a use sensation.

Examples of the fatty acid may include caprylic acid, capric acid, lauric acid, myristic acid, palmitic acid, stearic acid, behenic acid, oleic acid, linoleic acid, linolenic acid, isostearic acid, coconut oil fatty acid, arachidonic acid, and undecylenic acid. Among them, examples thereof may include lauric acid, myristic acid, palmitic acid, stearic acid, behenic acid, oleic acid, linoleic acid, linolenic acid, and isostearic acid, in terms of the viscosity stability and a use sensation. Each of these may be used singly or in combination of two or more thereof.

The content of the fatty acid is preferably from 0.01% by mass to 20% by mass, more preferably from 0.5% by mass to 10% by mass, and still more preferably from 0.5% by mass to 5% by mass, with respect to the total mass of the cosmetic. When the content of the fatty acid is 0.01% by mass or more, the viscosity stability of the cosmetic tends to be improved, and when the content is 20% by mass or less, the dispersibility of the composite powder tends to be improved.

<Higher Alcohol>

The cosmetic may contain a higher alcohol. By inclusion of a higher alcohol, the viscosity stability and a use sensation can be further improved.

The higher alcohol means an aliphatic alcohol having a total carbon number of 12 or more. The higher alcohol is a higher alcohol having a total carbon number of preferably from 12 to 24, more preferably from 8 to 20, and still more preferably from 10 to 18. Examples of the higher alcohol may include capryl alcohol, decyl alcohol, lauryl alcohol, myristyl alcohol, palmityl alcohol, cetostearyl alcohol, stearyl alcohol, behenyl alcohol, oleyl alcohol, isostearyl alcohol, octyldodecanol, hexyldecanol, jojoba alcohol, and coconut alcohol. Each of these may be used singly or in combination of two or more thereof.

The content of the higher alcohol is preferably from 0.01% by mass to 20% by mass, more preferably from 0.5% by mass to 10% by mass, and still more preferably from 0.5% by mass to 5% by mass, with respect to the total mass of the cosmetic. When the content of the higher alcohol is 0.01% by mass or more, the viscosity stability tends to be improved. When the content is 20% by mass or less, the dispersibility of the composite powder tends to be improved.

<Oil Absorbing Component>

The cosmetic may contain an oil absorbing powder. By inclusion of an oil absorbing powder, the viscosity stability of the cosmetic can be improved.

The oil absorbing powder in the invention denotes a water insoluble powder having an oil absorption in which squalane can be adsorbed at 25° C. in an amount of 30% by mass or more of the dead weight of powder.

As the measuring method of oil absorption, a known method may be used. The oil absorption can be measured, for example, by: placing 1 g of oil absorbing powder on a glass plate; kneading the oil absorbing powder using a spatula while dropping squalane in small steps; taking the time point at which the entire oil absorbing powder is in paste form as the end point; and taking the squalane amount (ml) per 1 g of oil absorbing powder at this time as the oil absorption.

As such an oil absorbing powder, examples thereof may include at least one powder selected from the group consisting of a porous silica powder, a crosslinked silicone powder, a porous nylon powder, a polymethyl methacrylate powder, and corn starch.

Examples of the porous silica powder include silica, silica silylate, dimethyl silica silylate, and silica dimethicone silicate. Preferable examples thereof include silica, from the viewpoint of viscosity stability. Examples of commercially available products thereof include SUNSPHERE H-31/H-32/H-33/H-51/H-52/H-53/H-121/H-122/and H-201 (manufactured by ASAHI GLASS CO., LTD.), VM-2270 Aerogel Fine Particle (manufactured by Dow Corning Toray Co., Ltd), HDK (registered trademark) H2000, HDK (registered trademark) H15, HDK (registered trademark) H18, HDK (registered trademark) H20, and HDK (registered trademark) H30, (manufactured by wacker asahikasei silicone co., ltd.), SYLOPURE (manufactured by FUJI SILYSIA CHEMICAL LTD.), TOKUSIL (manufactured by Tokuyama Corporation), and Microbead silica gel (Fuji Davison Chemical Ltd.).

Examples of the crosslinked silicone powder include a silicone gel powder, a silicone rubber powder, a silicone resin powder, and a silicone elastomer, and these can be used without distinguishing from one another. As the crosslinked silicone powder, a (dimethicone/vinyl dimethicone) crosspolymer, a (dimethicone/bis-isobutyl PPG-20) crosspolymer, a dimethicone crosspolymer, a (PEG-10/lauryl dimethicone) crosspolymer, a (PEG-10 dimethicone/vinyl dimethicone) crosspolymer, a (PEG-15/lauryl dimethicone) crosspolymer, a (PEG-15/lauryl polydimethylsiloxyethyl dimethicone) crosspolymer, a (diphenyl dimethicone/vinyl diphenyl dimethicone/silsesquioxane) crosspolymer, a (dimethicone/bis-isobutyl PPG-20) crosspolymer, a (dimethicone/vinyl trimethylsiloxysilicate) crosspolymer, a (dimethicone/phenyl vinyl dimethicone) crosspolymer, a (vinyl dimethicone/lauryl dimethicone) crosspolymer, a (vinyl dimethicone/methicone silsesquioxane) crosspolymer, a (lauryl polydimethylsiloxyethyl dimethicone/bis-vinyl dimethicone) crosspolymer, and the like are preferable, and a (dimethicone/vinyl dimethicone) crosspolymer or dimethicone crosspolymer is more preferable, from the viewpoint of viscosity stability of the cosmetic.

Examples of commercially available products of the silicone gel powder include KSG-15/16/1610, KSG-18A, KSG-41, KSP-100/101/102/105, KSP-300, 441/411, KSG-41/42/43/44, and KSG-240/310/320/330/340/710/320Z/350Z (manufactured by Shin-Etsu Chemical Co., Ltd). Examples of commercially available products of the silicone rubber powder include TREFIL E-506C, E-508, 9701 Cosmetic Powder, 9702 Powder, 9027/9040/9041/9045/9046/9041/9546 Silicone Elastomer Blend, EP-9215/EP-9216 TI/EP- 9289 LL/EP-9293 AL, EL-8040 ID Silicone Organic Blend (manufactured by Dow Corning Toray Co., Ltd.), Wacker-Belsil (registered trademark) RG 100 (manufactured by wacker asahikasei silicone co., ltd.), and NIKKOL SIL-BLEND-91 (manufactured by Nikko Chemicals Co., Ltd).

Examples of the porous nylon powder include nylon, nylon-6, nylon-11, nylon-12, a nylon-12/6/66 copolymer, nylon-6/12, and nylon-66. From the viewpoint of viscosity stability of the cosmetic, nylon-6, nylon-12, and the like are preferable.

Examples of commercially available products thereof include TR-1, TR-2, and SP-500 (manufactured by TORAY INDUSTRIES INC.), POMP 605 and POMP 610 (manufactured by UBE INDUSTRIES LTD.), and NYLON POWDER (manufactured by NIKKO RICA CORPORATION).

As the polymethyl methacrylate (hereinafter, it is also simply referred to as "PMMA") powder, a methyl methacrylate crosspolymer, a (methyl methacrylate/glycol dimethacrylate) crosspolymer, a (methyl methacrylate/acrylonitrile) copolymer, a (polymethyl methacrylate/dimethyl polysiloxane graft acrylic resin) copolymer, and an (ethylhexyl acrylate/methyl methacrylate) copolymer and the like are also included, in addition to PMMA.

Examples of commercially available products thereof include TECHPOLYMER (manufactured by SEKISUI PLASTICS CO., LTD.) and MATSUMOTO MICROSPHERE (manufactured by Matsumoto Yushi-Seiyaku Co., Ltd).

As the corn starch, DRY FLO PURE (manufactured by Akzo Nobel), and the like can be used.

In addition, as the oil absorbing powder, a porous polymer formed from styrene/stearyl methacrylate/divinylbenzene or the like, a hydrogenated (styrene/isoprene) copolymer, a (butylene/ethylene/styrene) copolymer, a (styrene/acrylamide) copolymer, a (ethylene/propylene/styrene) copolymer, a clay mineral, bentonite, synthetic phlogopite, a polyamide resin, and flaky titanium oxide can also be used. Examples of commercially available products thereof include LUXELEN D (manufactured by NIHONKOKEN Co., Ltd.), TIPAQUE CR-50 (manufactured by ISHIHARA SANGYO KAISHA, LTD.), PIONEER GEL 12 PAO (manufactured by Hansen & Rosenthal KG), Jojoba Glaze HV/LV (manufactured by Nikko Chemicals Co., Ltd.), Yodosol GH41F (manufactured by Akzo Nobel) and Kunipia F/G (manufactured by KUNIMINE INDUSTRIES CO., LTD.).

As the oil absorbing powder, a (dimethicone/vinyl dimethicone) crosspolymer, a dimethicone crosspolymer, and PMMA are preferable, and a (dimethicone/vinyl dimethicone) crosspolymer and PMMA are still more preferable, from the viewpoint of improving the viscosity stability and a use sensation of the cosmetic.

In the cosmetic according to the invention, one of the respective components described above may be used singly or two or more thereof may be used in combination, as the oil absorbing powder.

The particle diameter of the oil absorbing powder is not particularly limited, and the volume average particle diameter thereof is preferably from 0.005 µm to 30 µm, more preferably from 0.01 µm to 30 µm, and still more preferably from 0.1 µm to 30 µm, from the viewpoint of improving a use sensation. When the volume average particle diameter is 0.005 µm or more, a use sensation is improved without squeaky feel of skin at the time of use. In addition, when the volume average particle diameter is 30 µm or less, the surface area per unit weight of the oil absorbing powder does not become too small, decrease in oil absorption speed does not occur, and adhesion to skin is preserved. The volume average particle diameter can be measured with various commercially available particle size distribution meters or the like, and a particle size distribution meter adopting a dynamic light scattering method is used, in terms of particle size range and ease of measurement. As a commercially available measuring apparatus using dynamic light scattering, examples thereof include Nanotrac UPA (manufactured by NIKKISO CO., LTD.), Dynamic Light Scattering Particle Size Analyzer LB-550 (manufactured by HORIBA Ltd.), and Particle Size Analyzer for Concentrated System FPAR-1000 (manufactured by OTSUKA ELECTRONICS CO., LTD.).

The volume average particle diameter of the oil absorbing powder in the invention is the value measured using Particle Size Analyzer for Concentrated System FPAR-1000 (manufactured by OTSUKA ELECTRONICS CO., LTD). Specifically, the value measured according to the following manner is adopted.

That is, the method of measuring the oil absorbing powder is that the measurement is performed by diluting the oil absorbing powder with dimethicone so as to have a concentration of 1% by mass and using a quartz cell. The particle diameter can be determined as a volume average diameter when the sample refractive index is set as 1.600, the dispersion medium refractive index is set as 1.000 (dimethicone), and the viscosity of dispersion medium is set as the viscosity of dimethicone.

The content of the oil absorbing powder is preferably from 0.01% by mass to 20% by mass, more preferably from 0.05% by mass to 15% by mass, and still more preferably from 0.1% by mass to 10% by mass, with respect to the total mass of the cosmetic. When the content of the oil absorbing powder is 0.01% by mass or more, the viscosity stability tends to be improved, and when the content is 20% by mass or less, the feel tends to be improved.

The content of the oil absorbing powder is preferably from 0.01% by mass to 90% by mass, more preferably from 0.05% by mass to 50% by mass, further more preferably from 0.1% by mass to 20% by mass, and still more preferably from 0.1% by mass to 10% by mass, with respect to the total mass of the composite powder, from the viewpoint of improving the viscosity stability.

<Other Components>

The cosmetic may contain an ultraviolet absorber besides 4-tert-butyl-4-methoxybenzoylmethane described above. As such a ultraviolet absorber, any known oil soluble or water soluble ultraviolet absorber can be used.

Examples of the oil soluble ultraviolet absorber may include para-aminobenzoic acid, methyl para-aminobenzoate, glyceryl para-aminobenzoate, amyl para-dimethylaminobenzoate, octyl para-dimethylaminobenzoate, ethylene glycol salicylate, phenyl salicylate, octyl salicylate, butylphenyl salicylate, homomethyl salicylate, octyl methoxycinnamate, ethoxyethyl methoxycinnamate, ethylhexyl methoxycinnamate, glyceryl monoethylhexanoate dimethoxycinnamate, hydroxymethoxybenzophenone, dihydroxydimethoxybenzophenone, butyl methoxy benzoyl methane, and octyltriazone.

Examples of the water soluble ultraviolet absorber include a benzophenone-based ultraviolet absorber such as 2,4-dihydroxy benzophenone or 2,2'-dihydroxy-4-methoxy benzophenone; a benzimidazole-based ultraviolet absorber such as phenylbenzimidazole-5-sulfonic acid and a salt thereof, or phenylenebisbenzimidazole tetrasulfonic acid and a salt thereof; urocanic acid, urocanic acid ethyl ester, 2,2-(1,4-phenylene)bis-(1H-benzimidazole-4,6-disulphonic acid), and terephthalylidene dicamphor sulfonic acid.

The content of the ultraviolet absorber other than 4-tert-butyl-4-methoxybenzoylmethane is preferably from 0.001% by mass to 30% by mass, more preferably from 0.01% by mass to 20% by mass, and still more preferably from 0.1% by mass to 10% by mass, with respect to the total mass of the cosmetic, in terms of complementing the ultraviolet protection performance.

The total amount of ultraviolet absorber in the cosmetic is preferably from 0.001% by mass to 70% by mass, more preferably from 0.01% by mass to 50% by mass, and still more preferably from 0.1% by mass to 30% by mass, with respect to the total mass of the cosmetic, in terms of a use sensation.

The cosmetic may contain a volatile oil component as a solvent. By inclusion of a volatile oil component, feel of stickiness is reduced, therefore it is preferable.

The volatile oil component means a component having a boiling point in a range of from 60° C. to 260° C. under normal pressure. As the volatile oil component used in the invention, examples thereof include a volatile silicone-based oil and a volatile hydrocarbon-based oil.

Examples of the volatile silicone-based oil include a chain polysiloxane such as dimethylpolysiloxane (1.5 cs [$1.5 \times 10^{-6}$ m$^2$/s]), dimethylpolysiloxane (10 cs) (dimethicone 10 CS), methylphenylpolysiloxane, or methylhydrogenpolysiloxane; a cyclic polysiloxane such as cyclopentasiloxane, octamethylcyclotetrasiloxane, decamethylcyclopentasiloxane, dodecamethylcyclohexasiloxane, or tetramethyltetrahydrogencyclotetrasiloxane; and caprylyl methicone. Examples of commercially available products thereof include KF 96L-0.65, KF 96L-1, KF 96L-1.5, and KF 995 (manufactured by Shin-Etsu Chemical Co., Ltd.), SH 200-1cs, SH 200-1.5cs, SH 200-2cs, 2-1184 Fluid, SH 245 Fluid, DC 246 Fluid, DC 345 Fluid, and SS 3408 (manufactured by Dow Corning Toray Co., Ltd), and TSF 404, TSF 405, and TSF 4045 (manufactured by Momentive Performance Materials Inc).

As the volatile hydrocarbon-based oil, any of a linear volatile hydrocarbon-based oil and a branched volatile hydrocarbon-based oil may be used. Examples of such a volatile hydrocarbon-based oil include a C8 to C16 isoalkane (it is also known as isoparaffin) such as isodecane, isododecane, and isohexadecane. Examples of commercially available product thereof include Isopar (registered trademark) A, ISOPAR C, ISOPAR D, ISOPAR E, ISOPAR G, ISOPAR H, ISOPAR K, ISOPAR L, and ISOPAR M (manufactured by Exxon Mobil Corporation), SHELLSOL (registered trademark) 71 (manufactured by Shell), SALTROL (registered trademark) 100, SALTROL 130, and SALTROL 220 (manufactured by Philips), ISOSOL (registered trademark) 400 (manufactured by Nippon Petrochemicals Co., Ltd.), Parleam (registered trademark) 4 (manufactured by NOF CORPORATION), IP Solvent (registered trademark) 1620 and IP Solvent 2028 (manufactured by Idemitsu Kosan Co., Ltd.), Isohexadecane and Tetraisobutane 90 (manufactured by Bayer AG), and PERMETHYL (registered trademark) 99A, PERMETHYL 101A, and PERMETHYL 102A (manufactured by Presperse LLC).

One of the volatile oil components may be used singly, or two or more thereof may be used in combination.

The content of the volatile oil component is preferably from 0.001% by mass to 60% by mass, more preferably from 0.01% by mass to 40% by mass, and still more preferably from 0.1% by mass to 20% by mass, with respect to the total mass of the cosmetic, in terms of a use sensation.

The cosmetic may contain a polyhydric alcohol. By inclusion of a polyhydric alcohol, a use sensation (moisture retaining property) can be improved.

Examples of the polyhydric alcohol may include glycerin, 1,3-butanediol (1,3-BG), ethylene glycol, and a polysaccharide such as reduced starch syrup, sucrose, erythritol, xylitol, glucose, galactose, sorbitol, maltotriose, or trehalose. These may be used singly, or two or more thereof may be used in combination.

The cosmetic may contain other components, which are generally used for cosmetics, based on the form of emulsion or the intended use. Examples of such other components may include a water soluble organic solvent such as ethanol, a chelating agent, a skin brightening agent, a moisturizer, an antioxidant, a thickener, a coloring agent, a preservative, a perfume, various oil components, and various aqueous components.

The cosmetic of the invention can be produced by appropriately blending the respective components described above to prepare a W/O type or O/W type emulsified composition by a typical method.

The form of the cosmetic is not particularly limited, and examples thereof include skin care cosmetics such as skin toner (lotion), milky lotion, cream, eye cream, serum, massage materials, pack materials, ointment, cream, and body cream, and makeup cosmetics such as makeup base.

It is particularly preferable that the cosmetic of the invention is used as a sunscreen cosmetic due to the high ultraviolet shielding performance and a favorable use sensation.

EXAMPLES

Hereinafter, the invention is described in detail with reference to Examples. However, the invention is not limited thereto.

Example 1

After sufficiently dispersing (1) cyclopentasiloxane, (2) HXMT-100ZA (manufactured by TAYCA Corporation, average primary particle diameter: 15 nm, average particle diameter: 15 nm) and (3) dimethicone 10CS at room temperature using a disperser so as to have the final concentration (% by mass) shown in Table 1 below, (4) PEG-9 polydimethylsiloxane ethyl dimethicone (manufactured by Shin-Etsu Chemical Co., Ltd.), (5) sorbitan oleate as a sorbitan fatty acid ester (NIKKOL SO-10V (manufactured by Nikko Chemicals Co., Ltd.)), (6) a (dimethicone/vinyl dimethicone) crosspolymer (KSG-16 having a volume average particle diameter of 5 µm, and manufactured by Shin-Etsu Chemical Co., Ltd.), and (7) a (dimethicone/(PEG-10/15) crosspolymer (KSG-210 manufactured by Shin-Etsu Chemical Co., Ltd.) were mixed by agitation to perform homogenization, thereby obtaining the oil phase component. Subsequently, a predetermined amount of (8) ethanol, (9) 1,3-butylene glycol (1,3-BG) and (11) water (a portion thereof) were weighed, mixed by agitation at room temperature and homogenized, thereby obtaining the aqueous phase component. Emulsification was performed by gradually adding the aqueous phase component to the oil phase component while agitating the oil phase component using a homomixer, (10) phenoxyethanol was added thereto, and the homogenization was performed by adding the rest of water, thereby obtaining emulsion 1 containing the respective components in the blending amounts shown in Table 1 below.

Examples 2 to 5, and Comparative Examples 1 to 3

Emulsions 2 to 5 according to Examples 2 to 5 and emulsions 6 to 8 according to Comparative Examples 1 to 3 were obtained in the same manner as in Example 1 using the components (1) to (11) above, except that the kind or amount (% by mass) of the sorbitan fatty acid ester of the component (5) was changed to those shown in Table 1. In a case where the sorbitan fatty acid ester selected was solid at room temperature, the sorbitan fatty acid ester was dissolved by heating in advance, and then mixed into the dispersion of (1) to (3), and (4), (6), and (7), at 80° C., emulsification was performed by gradually adding the aqueous phase component that was heated to 80° C., subsequently, (10) was added thereto, and homogenization was performed by adding the rest of water, thereby obtaining the emulsion containing the respective components in the blending amounts shown in Table 1 below.

<Evaluation>

(1) Evaluation of Viscosity Stability

The viscosity (initial viscosity) of the emulsions 1 to 8 was measured with a BL-type viscometer at room temperature (25° C.) after the emulsions from 1 to 8 were prepared and left to stand for one day. Thereafter, the emulsions were put into a high temperature bath at 40° C., and two days later, the viscosity (viscosity over time) at 25° C. was measured using the BL-type viscometer (manufactured by TOKI SANGYO CO., LTD.).

The rate of change of viscosity with respect to the initial value was defined as the index for evaluating the stabilization, which indicates the extent to which the increase or decrease in viscosity from the initial value was suppressed, by the following Expression. The results are shown in Table 1.

Rate of change of viscosity with respect to initial value (%)=[(viscosity over time−initial viscosity)/(initial viscosity)]×100

The viscosity stability was evaluated as (A) "excellent" in a case where the rate of change of viscosity was ±20% or less. The viscosity stability was evaluated as (C) "inappropriate" in a case where the rate of change of viscosity was more than ±20%, or separation of the aqueous phase and oil phase occurred. The results are shown in Table 1.

(2) Evaluation of Use Sensation

Each of the emulsions obtained as described above was applied to the face of ten expert panelists, and the evaluation was performed with regard to the two criteria of spreading at the time of application and stickiness immediately after application, in five grades from outstanding (5 points) to extremely poor (1 point). The average value of the evaluation results of the ten expert panelists was taken, and then the evaluation was performed such that an average value of from 1 to less than 2 was ranked as C, an average value of from 2 to less than 3 was ranked as B, an average value of from 3 to less than 4 was ranked as A, and an average value of from 4 to 5 was ranked as S. The results are shown in Table 1.

(3) Overall Determination

Each of the emulsions was evaluated as (S) excellent as a commodity, (A) favorable as a commodity, (B) possible as a commodity, or (C) inappropriate as a commodity, based on the results of the items (1) and (2) described above. The results are shown in Table 1.

TABLE 1

| | Name of raw materials | Example 1 | Example 2 | Example 3 | Example 4 | Example 5 | Comparative Example 1 | Comparative Example 2 | Comparative Example 3 |
|---|---|---|---|---|---|---|---|---|---|
| (1) | Cyclopentasiloxane | 26% | 26% | 26% | 26% | 26% | 30% | 26% | 26% |
| (2) | HXMT-100ZA | 13% | 13% | 13% | 13% | 13% | 13% | 13% | 13% |
| (3) | Dimethicone 10CS | 7% | 7% | 7% | 7% | 7% | 7% | 7% | 7% |
| (4) | PEG-9 polydimethylsiloxy-ethyl dimethicone | 4% | 4% | 4% | 4% | 4% | — | 4% | 4% |
| (5) | Sorbitan fatty acid ester | | | | | | | | |
| | Sorbitan oleate | 4% | | | | | | 4% | |
| | Sorbitan sesquicaprylate | | | | | | | | |
| | Sorbitan sesquistearate | | 4% | | | | | | |
| | Sorbitan sesquioleate | | | 4% | | | | | |
| | Sorbitan sesquiisostearate | | | | 4% | | | | |
| | Sorbitan trioleate | | | | | 4% | | | |
| | PEG-6 sorbitan oleate | | | | | | | | 4% |
| (6) | (Dimethicone/vinyl dimethicone) crosspolmyer | 2% | 2% | 2% | 2% | 2% | 2% | 2% | 2% |
| (7) | (Dimethicone/(PEG-10/15)) crosspolymer | 2% | 2% | 2% | 2% | 2% | 2% | 2% | 2% |
| (8) | Ethanol | 8% | 8% | 8% | 8% | 8% | 8% | 8% | 8% |
| (9) | 1,3-BG | 4% | 4% | 4% | 4% | 4% | 4% | 4% | 4% |
| (10) | Phenoxyethanol | 0.15% | 0.15% | 0.15% | 0.15% | 0.15% | 0.15% | 0.15% | 0.15% |
| (11) | Water | total 100% | total 100% | total 100% | total 100% | total 100% | total 100% | total 100% | total 100% |
| Evaluation | Rate of change of viscosity (%) | −13 | −8 | −16 | −15 | −3 | −36 | Separated | Separated |
| | Viscosity stability | A | A | A | A | A | C | C | C |
| | Spreading/stickiness | A/A | A/S | S/S | S/S | A/A | B/B | —/— | —/— |
| | Overall | A | A | S | S | A | B | C | C |

As shown in Table 1, all of the emulsions 1 to 5 according to Examples 1 to 5 exhibited a small rate of change of viscosity and excellent viscosity stability, compared with the emulsions 6 to 8 according to Comparative Examples 1 to 3, and in addition, the results of the evaluation of use sensation with respect to spreading and stickiness were excellent.

In particular, the sensory evaluation was particularly high for Examples 3 and 4, in which a sorbitan fatty acid ester containing a linear unsaturated aliphatic group or a branched saturated aliphatic group was used.

In contrast, it was understood that the viscosity stability was significantly impaired in each of the emulsions of: Comparative Example 1 in which a sorbitan fatty acid ester was not contained; Comparative Example 2 in which a sorbitan fatty acid ester having a fatty acid chain having 8 carbon atoms was used; and Comparative Example 3 in which a sorbitan fatty acid ester having a hydrophilic group such as polyoxyethylene (PEG) was used.

Examples 6 and 7

A W/O type emulsified UV milk (Table 2) and an O/W type emulsified UV milk (Table 3) are formulated according to the formulae shown in Table 2 and Table 3, respectively. The numerical values in Table 2 and Table 3 mean "% by mass". HXMT-100ZA (manufactured by TAYCA Corporation) was used as the composite powder of "1. Titanium oxide and t-butyl methoxydibenzoylmethane" in Table 2 and Table 3. Moreover, PMMA manufactured by Matsumoto Yushi-Seiyaku Co., Ltd. is used as PMMA. The volume average particle diameter of each of the oil absorbing powders used was 5 μm.

TABLE 2

| 1 | Titanium oxide | 15% |
| | t-Butyl methoxydibenzoylmethane | |
| 2 | Cyclopentasiloxane | 17% |
| 3 | Dimethicone | 10% |
| 4 | PEG-9 polydimethylsiloxyethyl dimethicone | 4% |
| 5 | Diphenylsiloxy phenyl trimethicone | 3% |
| 6 | Ethanol | 3% |
| 7 | 1,3-BG | 3% |
| 8 | Sorbitan sesquioleate | 1% |
| 9 | Isostearic acid | 0.50% |
| 10 | (Dimethicone/(PEG-10/15)) crosspolymer | 0.50% |
| 11 | (Dimethicone/vinyl dimethicone) crosspolymer | 0.50% |
| 12 | (Methyl methacrylate/glycol dimethacrylate) crosspolymer | 0.50% |
| 13 | Phenoxy ethanol | 0.30% |
| 14 | Water | total 100% |

TABLE 3

| 1 | Titanium oxide | 9% |
| | t-Butyl methoxydibenzoylmethane | |
| 2 | Isotridecyl isononanoate | 5% |
| 3 | Ethanol | 5% |
| 4 | Octyldodecyl myristate | 4% |
| 5 | 1,3-BG | 4% |
| 6 | Ethylhexyl methoxycinnamate | 4% |
| 7 | Cyclopentasiloxane | 4% |
| 8 | (Butyl acrylate/glycol dimethacrylate) crosspolymer | 1% |
| 9 | PEG-60 hydrogenated castor oil | 1% |
| 10 | Squalane | 1% |
| 11 | PMMA | 1% |
| 12 | Sorbitan sesquioleate | 0.50% |
| 13 | Phenoxy ethanol | 0.30% |
| 14 | Water | total 100% |

Both of the W/O type emulsified UV milk (Table 2) and the O/W type emulsified UV milk (Table 3) are cosmetics that exhibit a high ultraviolet shielding effect, excellent viscosity stability, and an excellent use sensation since both of the W/O type emulsified UV milk (Table 2) and the O/W type emulsified UV milk (Table 3) are cosmetics containing the composite powder, and the sorbitan fatty acid ester according to the invention.

As described above, according to the invention, a cosmetic exhibiting a high ultraviolet shielding effect, excellent viscosity stability, and an excellent use sensation can be provided.

The entirety of the disclosure of Japanese Patent Application No. 2011-239728 is incorporated herein by reference. All documents, patent applications, and technical standards described herein are incorporated by reference to the same extent as a case in which each of the documents, patent applications, and technical standards is individually and specifically incorporated by reference herein. The foregoing description with regard to the exemplary embodiments of the invention is for the purpose of illustration and explanation, and is not intended to be exhaustive or limit the invention to the precise forms disclosed. Although it is clear, it is appreciated by those skilled in the art that many modifications or changes may be made in these embodiments without departing from the principles and spirit of the invention. The embodiments described above are selected in order to best explain the principles of the invention and practical applications, to provide various embodiments applicable to particular uses estimated or various modifications, and to aid those skilled in other arts in understanding the invention. It is intended that the scope of the invention is defined in the appended claims and their equivalents.

The invention claimed is:

1. A cosmetic, comprising:
a composite powder containing titanium oxide and 4-tert-butyl-4-methoxybenzoylmethane and having an average particle diameter of less than 1 μm; and
a sorbitan fatty acid ester represented by the following Formula (I):

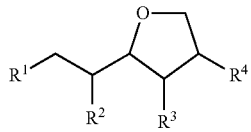

wherein, in Formula (I), $R^1$ to $R^4$ each independently represent $-(CH_2)_n COOH$, $-(CH_2)_n OH$, $-R^5$, or $-OR^6$; $R^5$ represents an aliphatic group having from 1 to 22 carbon atoms; $R^6$ represents an acyl group having from 10 to 22 carbon atoms; n represents 0 or an integer from 1 to 29; and at least one of $R^1$ to $R^4$ represents $-OR^6$.

2. The cosmetic according to claim 1, wherein the titanium oxide comprises a surface treatment layer containing the 4-tert-butyl-4-methoxybenzoylmethane on a surface thereof.

3. The cosmetic according to claim 1, wherein $R^6$ in Formula (I) represents an acyl group having from 10 to 20 carbon atoms.

4. The cosmetic according to claim 1, wherein the sorbitan fatty acid ester includes two or more sorbitan fatty acid esters each represented by Formula (I).

5. The cosmetic according to claim 1, wherein $R^6$ in Formula (I) is a group selected from the group consisting of a branched saturated aliphatic acyl group, a linear unsaturated aliphatic acyl group, and a branched unsaturated aliphatic acyl group, and a total carbon number of the acyl group is from 14 to 18.

6. The cosmetic according to claim 1, wherein the sorbitan fatty acid ester includes two or more sorbitan fatty acid esters each represented by Formula (I), in each of which the number of $-OR^6$ is different from one another.

7. The cosmetic according to claim 1, wherein $R^6$ in Formula (I) represents a branched saturated aliphatic acyl group having a total carbon number of from 14 to 18 or a linear unsaturated aliphatic acyl group having a total carbon number of from 14 to 18.

8. The cosmetic according to claim 1, wherein the sorbitan fatty acid ester is at least one selected from the group consisting of sorbitan sesquioleate and sorbitan sesquiisostearate.

9. The cosmetic according to claim 1, further comprising an oil absorbing powder.

10. The cosmetic according to claim 9, wherein the oil absorbing powder is at least one powder selected from the group consisting of a porous silica powder, a crosslinked silicone powder, a porous nylon powder, a polymethyl methacrylate powder, and corn starch.

11. The cosmetic according to claim 1, wherein a content of the sorbitan fatty acid ester is from 0.01% by mass to 20% by mass with respect to a total mass of the cosmetic.

12. The cosmetic according to claim 1, wherein a content of the sorbitan fatty acid ester is from 0.0001 times to 150 times the amount on a mass basis with respect to a content of the composite powder.

13. The cosmetic according to claim 1, being a sunscreen cosmetic.

* * * * *